(12) United States Patent
Choi et al.

(10) Patent No.: US 8,492,739 B2
(45) Date of Patent: Jul. 23, 2013

(54) PROBE INSPECTION APPARATUS FOR TESTING FLAT PANEL DISPLAY

(75) Inventors: Youngseok Choi, Daejeon (KR); Seungwoo Jeong, Seoul (KR); Hoon Choi, Incheon (KR)

(73) Assignee: LG Display Co. Ltd., Seoul (KR)

( * ) Notice: Subject to any disclaimer, the term of this patent is extended or adjusted under 35 U.S.C. 154(b) by 679 days.

(21) Appl. No.: 12/533,775

(22) Filed: Jul. 31, 2009

(65) Prior Publication Data

US 2010/0155574 A1   Jun. 24, 2010

(30) Foreign Application Priority Data

Dec. 22, 2008 (KR) .................. 10-2008-0131488

(51) Int. Cl.
*G01N 21/86* (2006.01)
*G01J 3/50* (2006.01)

(52) U.S. Cl.
USPC ..................................... 250/559.04; 250/226

(58) Field of Classification Search
USPC ......... 250/221, 205, 578.1, 234, 239, 559.01, 250/559.04, 559.05, 559.07, 55, 9.08, 559.11, 250/559.39, 559.4; 356/237.1, 239.1, 239.3, 356/239.7, 237.2–237.5; 349/1, 192; 324/756.04, 756.03, 754.01, 754.05, 754.1, 324/755.01–755.04, 760.01, 760.02; 439/482

See application file for complete search history.

(56) References Cited

U.S. PATENT DOCUMENTS 7,083,304 B2 *  8/2006  Rhoads et al. ................. 362/293
7,859,274 B2 * 12/2010  Kim et al. ................. 324/754.21
2009/0021276 A1 *  1/2009  Boss et al. ..................... 324/761

FOREIGN PATENT DOCUMENTS

KR       10-0768912       * 10/2007

* cited by examiner

*Primary Examiner* — Pascal M Bui Pho
(74) *Attorney, Agent, or Firm* — Brinks Hofer Gilson & Lione

(57) ABSTRACT

This document relates to a probe inspection apparatus for testing a flat panel display. The probe inspection apparatus comprises a base plate, a stage placed over the base plate and configured to comprise a plurality of back light modules for supplying a rear surface of a substrate with light or heat or both, the substrate being seated in the stage, a probe pin configured to electrically come into contact with circuit patterns formed in the substrate and measure electrical properties of the circuit patterns, a probe head configured to support the probe pin and move in an X or Y axis, and an upper light source unit mounted on one side of the probe head and configured to irradiate light to the circuit patterns.

12 Claims, 11 Drawing Sheets

PROBE INSPECTION APPARATUS FOR TESTING FLAT PANEL DISPLAY

RELATED APPLICATIONS

This application claims the benefit of Korea Patent Application No. 10-2008-131488 filed on Dec. 22, 2008, which is incorporated herein by reference for all purposes as if fully set forth herein.

BACKGROUND

1. Field

This disclosure relates to a probe inspection apparatus for testing a flat panel display and, more particularly, to a probe inspection apparatus capable of measuring a change in the electrical properties of circuit patterns formed in the thin film transistor (hereinafter referred to as a 'TFT') substrate of a liquid crystal display.

2. Related Art

A variety of flat panel displays (FPDs) which are capable of reducing the disadvantages of a cathode ray tube (i.e., weight and volume) are recently emerging. The flat panel displays may comprise a liquid crystal display (LCD), a field emission display (FED), a plasma display panel (PDP), an electro-luminescent display, and so on. There is a tendency that, from among the displays, the liquid crystal display gradually finds various applications because of its light weight, slimness, low-power driving, etc.

A process of fabricating the liquid crystal display comprises a process of fabricating a rear substrate, a process of fabricating a front substrate, a process of coalescing the front and rear substrates, and the like. The front substrate comprises a mother substrate formed of a plurality of color filter substrates, and the rear substrate comprises a mother substrate formed of a plurality of TFT substrates.

In the TFT substrate, a plurality of horizontal lines and a plurality of vertical lines are formed to cross each other in a matrix form, and pixels, each having a transparent pixel electrode, are formed at the respective intersections of the vertical lines and the horizontal lines. TFT each coupled to the vertical line, the horizontal line, and the pixel electrode are formed in the respective pixels. The rear substrate in which the plurality of TFT substrates is formed experiences a test process and then coalesces with the front substrate. The coalesced front and rear substrates are cut into liquid crystal panels through a scribing process. A liquid crystal panel, a backlight unit, etc. are assembled in each liquid crystal panel, thereby constituting a liquid crystal module. Driving circuits are coupled to the liquid crystal module, thereby completing a liquid crystal display.

In a test process for the rear substrate during the process of fabricating the liquid crystal display, whether a circuit pattern (for example, a TFT) formed in the rear substrate is good or bad is determined by supplying an electrical test signal to the circuit pattern using a probe inspection apparatus. This circuit pattern test may be performed for the TFT substrate cut from the mother substrate (i.e., the rear substrate), but is generally performed for the mother substrate (i.e., the rear substrate) in order to increase the efficiency of a test. Hereinafter, the mother substrate (i.e., the rear substrate) is referred to as a substrate, for convenience of description.

In order to obtain a more accurate measurement value when the electrical properties of a circuit pattern are tested, the probe inspection apparatus requires a temperature and ambient condition similar to the actual operating condition of a circuit pattern in the liquid crystal module state. That is, the probe inspection apparatus is required to operate under such conditions as light and heat generated by the back light while the liquid crystal display operates.

The influence of light when a change in the characteristics of a circuit pattern is measured is described below. The electrical properties of a circuit pattern formed in the substrate are greatly influenced by a photo current. Here, the photo current refers to an electric current generated when the flow of an electric current of the circuit pattern is changed owing to a photoelectric effect in the case where the circuit pattern formed in the substrate is exposed to light. The photo current of a circuit pattern, generated by an illuminator such as a fluorescent lamp, is very different from that of a circuit pattern, generated by back light in the liquid crystal module state. Further, the luminance and color temperature of an illuminator, such as a fluorescent lamp, is very different from that of a back light. Accordingly, measurement information about the electrical properties through a conventional probe inspection apparatus is inevitably being used as only reference information. Since precise process management and measurement become necessary with the larger size of a liquid crystal display, a change in the photo current which had not been conventionally problematic has a great effect on the quality of a product. Accordingly, an illuminator capable of performing the same function as the back light is being required in a probe apparatus (i.e., an apparatus for testing the electrical properties of the substrate).

The effect of heat when a change in the characteristics of a circuit pattern is measured according to the application of an electrical signal is described below. As described above, in order to obtain more precise measurement values when the electrical properties of a circuit pattern formed in the substrate are tested, the same heat condition as that when a liquid crystal display operates has to be provided. Accordingly, a hot plate is conventionally provided in a probe inspection apparatus so that more precise measurement values can be obtained while the same temperature condition as that when the liquid crystal display operates is maintained. If the hot plate is used, however, not only noise is generated when the circuit pattern is heated, but also it is difficult to control a heating temperature for maintaining a change in the measurement temperature within a specific range. In other words, if it is sought to measure the heat characteristic of the circuit pattern, a very low electric current flowing through the circuit pattern has to be measured (10E-15A) while heat is applied to the circuit pattern by slowly (generally, −10 V to +30 V) raising voltage of the hot plate. It is, however, impossible to precisely measure a change in the heating characteristic of the circuit pattern due to noise generated upon heating because an electrical heating method is used. Further, in order to precisely measure the heating characteristic of the circuit pattern, a change in the measurement temperature has to be very small. However, a test apparatus using the above-described hot plate is difficult to control the change in the measurement temperature. This hot plate cannot be used to measure a change in the characteristic caused by light because it is formed of an opaque metal plate.

Consequently, since more precise process management and measurement for a liquid crystal display are required, a need to measure the electrical properties for the substrate in a state similar to that in which the liquid crystal display actually operates (i.e., a state in which heat and light are affected at the same time) comes to the forefront. However, the conventional probe inspection apparatus using the hot plate and the illuminator can be used to perform measurement using only heat or light. Further, the conventional probe inspection apparatus is problematic in that the reliability of measurement data and the convenience of measurement are low because a change in the characteristic resulting from heat and a change in the characteristic resulting from light are separately measured and the two characteristic change data are combined and used.

Moreover, the conventional probe inspection apparatus is used to measure only the electrical properties of a TFT in the state in which the TFT has been completed. Accordingly, the conventional probe inspection apparatus has problems in that a change in the characteristic of a TFT depending on a change in the channel width (W)/channel length (L) of the TFT (i.e., critical factors in an actual characteristic) cannot be known and characteristic analysis is therefore limited because it cannot measure a change in the W/L of a channel during a test process.

BRIEF SUMMARY

A probe inspection apparatus comprises a base plate, a stage placed over the base plate and configured to comprise a plurality of back light modules for supplying a rear surface of a substrate with light or heat or both, the substrate being seated in the stage, a probe pin configured to electrically come into contact with circuit patterns formed in the substrate and measure electrical properties of the circuit patterns, a probe head configured to support the probe pin and move in an X or Y axis, and an upper light source unit mounted on one side of the probe head and configured to irradiate light to the circuit patterns. The upper light source unit comprises light source arrays, a color filter plate placed on the light source arrays and configured to downwardly reflect light generated by the light source arrays, a light source support track into which the color filter plate is inserted and on which the light source arrays are mounted, and a light emission hole configured to introduce the reflected light to the circuit patterns.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE DRAWINGS AND THE PRESENTLY PREFERRED EMBODIMENTS

Hereinafter, implementations of this document will be described in detail with reference to the attached drawings.

Figure 1:
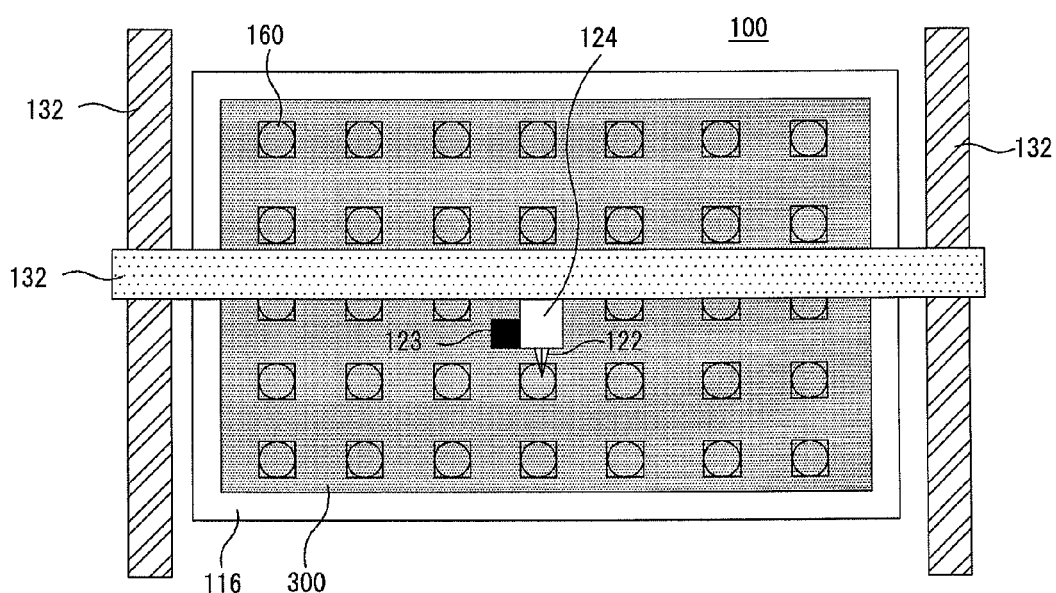
FIG. 1 is a plan view of a probe inspection apparatus according to an embodiment of this disclosure.
Figure 2:
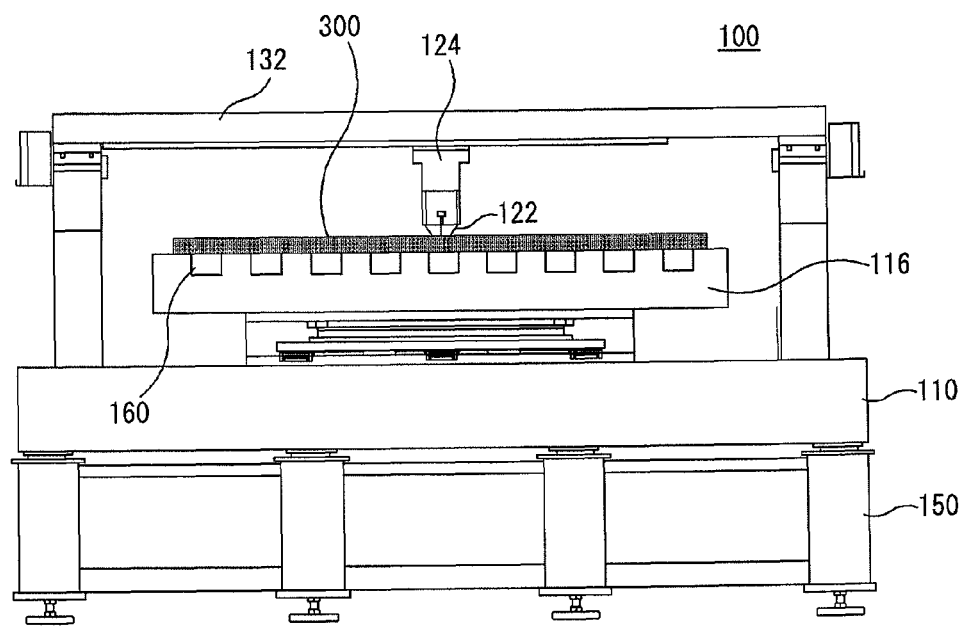
FIG. 2 is a cross-sectional view of the probe inspection apparatus according to an embodiment of this disclosure.

FIG. 1 is a plan view of a probe inspection apparatus according to an embodiment of this disclosure, and FIG. 2 is a cross-sectional view of the probe inspection apparatus according to an embodiment of this disclosure.

The probe inspection apparatus 100 according to this disclosure is configured to test a substrate for a liquid crystal display in which TFTs are formed at the respective intersections of horizontal lines and vertical lines. The probe inspection apparatus 100 comprises, as shown in FIGS. 1 and 2, comprises supporters 150 formed of respective poles, a base plate 110 fixed on the supporters, a stage 116 placed over the base plate 110 and having a substrate 300 (i.e., a target test object) mounted thereon, a probe pin 122 configured to electrically come into contact with TFTs formed in the substrate 300 and measure the electrical properties of the TFTs, a probe head 124 configured to mechanically support the probe pin 122 and move in the X or Y axis to make the probe pin 122 come into contact with each of the TFTs, and a plurality of linear motors 132 placed over the base plate 110 in order to move the probe head 124 in the X or Y axis.

The stage 116 is a table on which the substrate 300 (i.e., a target test object) is placed and is configured to mount thereon back light modules 160 for irradiate light to the substrate 300 in a test process. The back light modules 160 may be configured to emit only light or both light and heat. This is described in detail below with reference to FIGS. 3 and 4.

A control device (not shown) for driving and controlling the stage 116 and the linear motors 132 and a test device (not shown) for supplying the substrate 300 with an electrical test signal and also storing test results may be installed in an internal space surrounded by the supporters 150.

The base plate 110 may be formed of a granite surface plate or a casting surface place having a high degree of flatness. The stage 116 is placed over the base plate 110. The linear motors 132 are coupled to the poles supported by the base plate 110, and the probe head 124 coupled to the linear motors 132 moves in the X or Y axis over the substrate 300 placed over the stage 116.

An upper light source unit may be mounted on the probe head 124. When the TFT is operated in an actual liquid crystal module state, the TFT is greatly influenced by direct back light and also light reflected in a color filter. With this fact taken into consideration, the upper light source unit comprises light source arrays configured to generate light and a color filter plate placed on the light source arrays and configured to reflect light, irradiated from the light source arrays, toward the TFT. Accordingly, a similar environment to an actual driving state when the characteristics of the TFT are tested can be provided. This is described in detail later with reference to FIG. 7.

A microscope may also be attached to the probe head 124. The microscope provides a user with an environment in which, when a contact pad (several tens of μm) for the TFT formed in the substrate 300 is brought in contact with the probe pin 122, whether the contact pad and the probe pin are brought in contact with each other in position can be monitored. Further, the microscope may provide an image for the W/L of the TFT on which an electrical property test is being performed. Accordingly, the probe inspection apparatus 100 according this document can increase the accuracy of characteristic analysis using a correlation between the W/L of the TFT and the electrical property value of the TFT. This is described in detail later with reference to FIG. 10.

The probe inspection apparatus 100 having the above construction is configured to emit light or heat or both using the back light modules 160 mounted on the stage 116 and the upper light source unit mounted on the probe head 124 when the electrical properties for the substrate 300 are tested, so that the TFT formed in the substrate 300 can be provided with an environment similar to an actual liquid crystal module state. Accordingly, the reliability of measurement values for the electrical properties of the TFT can be increased.

Figure 3:
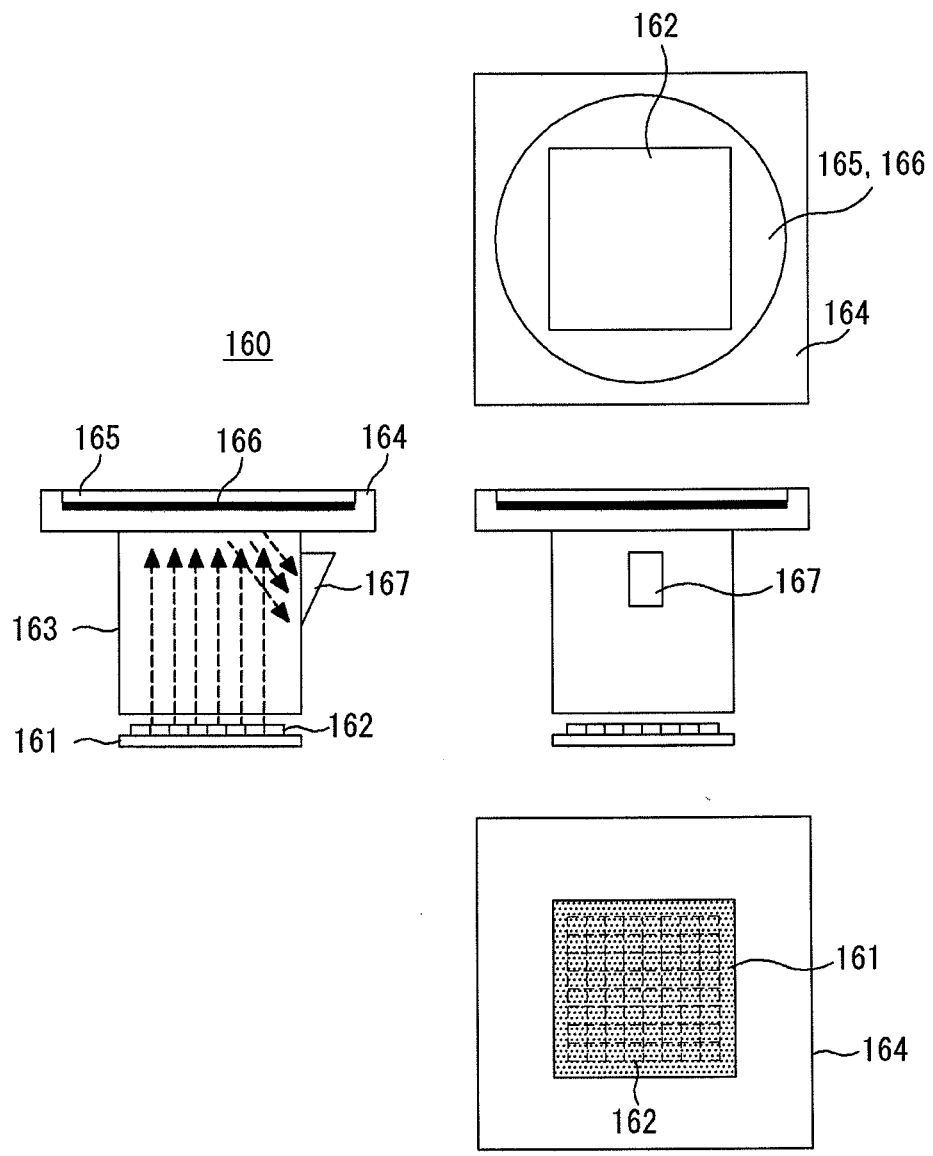
FIG. 3 shows an example of a back light module which is applied to this document and configured to emit only light.
Figure 4:
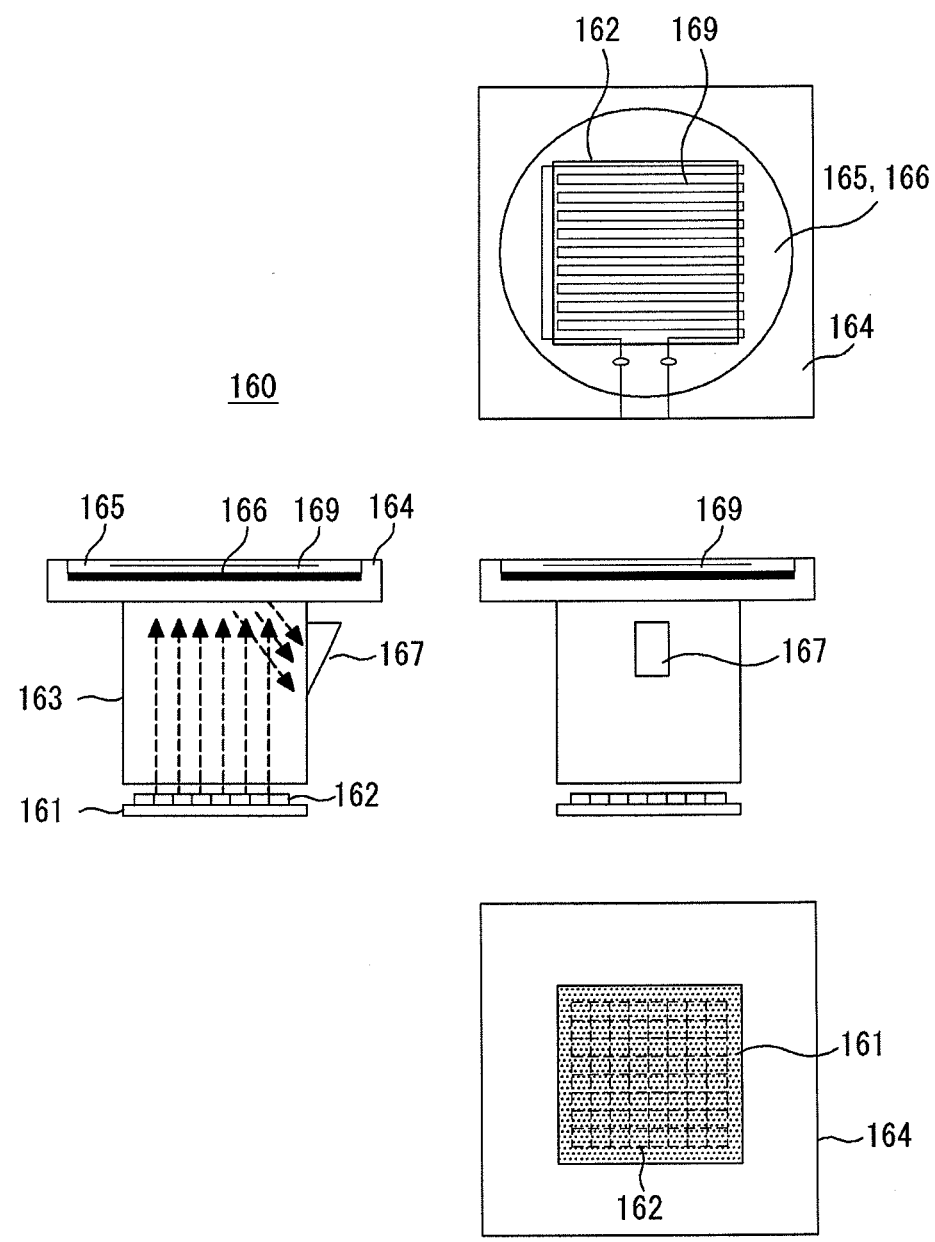
FIG. 4 shows another example of the back light module which is applied to this disclosure and configured to emit light and heat.

FIG. 3 shows an example of the back light module which is applied to this disclosure and configured to emit only light. FIG. 4 shows another example of the back light module which is applied to this disclosure and configured to emit light and heat.

This document provides the probe inspection apparatus 100 in which, when the electrical properties of the TFT formed in the substrate are tested, measurement can be performed in a state similar to an operating condition in an actual liquid crystal module state. However, in the case where it is necessary to measure the electrical properties of the TFT by providing only light, the back light module 160 shown in FIG. 3 may be used, and in the case where it is necessary to measure the electrical properties of the TFT by providing both light and heat, the back light module 160 shown in FIG. 4 may be used. The back light module 160 applied to this document may be fabricated in various models depending on the size of the substrate and luminance applied to the substrate. In particular, the back light module 160 may be fabricated without heating coils as shown in FIG. 3 so that only the light properties of the substrate for the liquid crystal display can be taken into consideration, and the back light module 160 having heating coils 169 built therein may be fabricated as shown in FIG. 4 so that the light and heat properties of the substrate for the liquid crystal display can be measured at the same time.

Referring to FIG. 3, the back light module 160 comprises a printed circuit board (hereinafter referred to as a 'PCB') 161 having a plurality of light sources 162 formed therein, a light-emitting tube 163 configured to provide a passage through which light generated from the light sources 162 passes, a light-emitting surface 165 having a spread sheet 166 for uniformly spreading light generated from the light sources 162 attached thereto, and a support frame 164 configured to support the light-emitting surface 165 on the light-emitting tube 163. Here, the light-emitting surface 165 may be made of transparent material, such as synthetic resin or glass. A photo sensor 167 for detecting the amount or luminance of light reflected from the spread sheet 166 or the light-emitting surface 165 may be further provided on one side of the light-emitting tube 163. The photo sensor 167 is described in detail later with reference to FIG. 8.

Referring to FIG. 4, the back light module 160 has the same construction as the back light module 160 shown in FIG. 3 except that the heating coils 169 configured to generate heat using an externally applied power source are further included in the light-emitting surface 165. The heating coils 169 may be implemented using metallic patterns formed by a vacuum deposition technology, etc. When the electrical properties of a TFT are tested, the heating coils 169 function to provide the substrate with heat. Since measurement of the electrical properties of the substrate for the liquid crystal display is very sensitive to electrical noise, an electric current may be applied to the heating coils 169 using a linear power, and the heating coils 169 may be controlled using an analog consecutive proportional-plus-integrate-plus-derivative (PID) control method. Here, the terminology 'linear power' refers to a DC power supplier having a less occurrence of ripples and noise. The terminology 'analog consecutive PID control method' refers to a method of controlling temperature using an electric current in order to minimize a temperature change. Although not shown in FIG. 4, the back light module 160 may further comprise a heat sensor in the light-emitting surface 165. The heat sensor is described in detail later with reference to FIG. 8.

The light sources 162 applied to the back light module 160 shown in FIGS. 3 and 4 requires the following characteristics. The light sources 162 must have a high luminance and uniformity, a color temperature and other optical properties which are similar to those of back light applied to a current liquid crystal display, and free control of the intensity of radiation. It is also required that the brightness of the light sources 162 be stabilized within a short time, and the light sources 162 be able to consistently maintain a designated brightness and have no change in the brightness resulting from a lift span. Accordingly, any kind of the light sources 162 having the above characteristics may be used. For example, a light-emitting diode may be used as the light sources 162.

Figure 5:
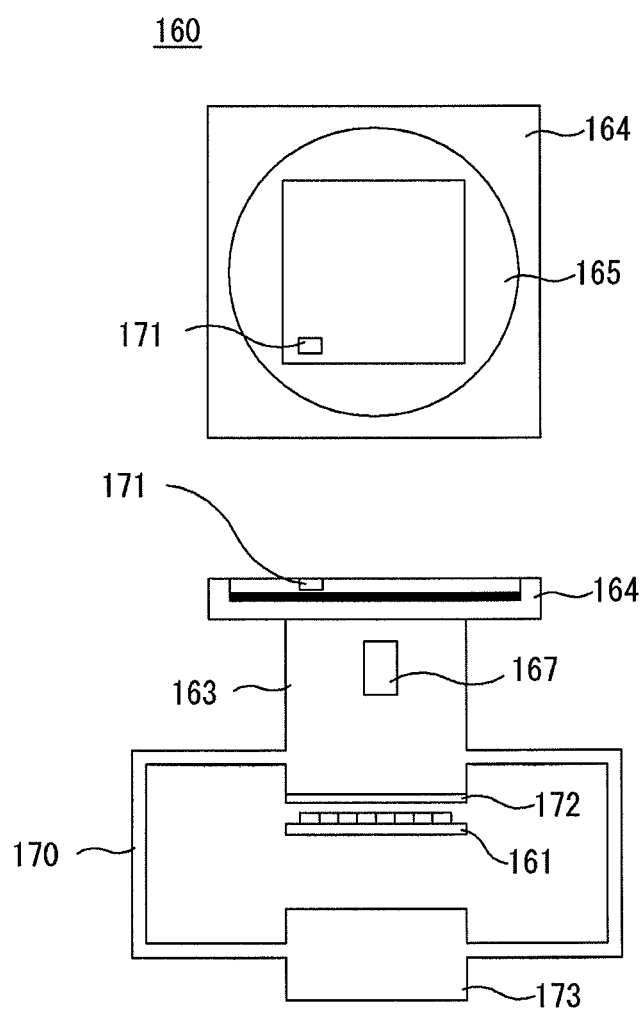
FIG. 5 shows yet another example of the back light module which is applied to this disclosure and configured to emit heat using a heat gun.
Figure 6:
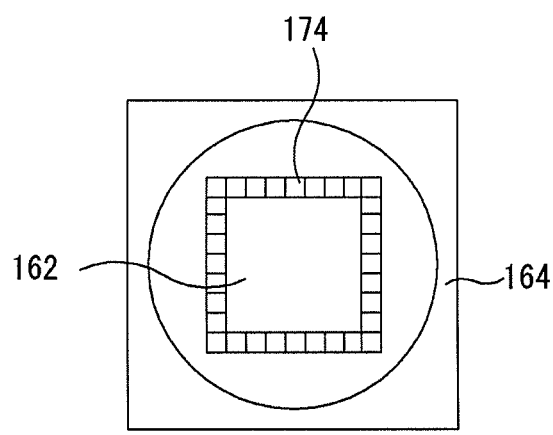
FIG. 6 shows further yet another example of the back light module which is applied to this disclosure and configured to use ultraviolet/infrared light-emitting diodes as light-emitting diodes.
Figure 6:
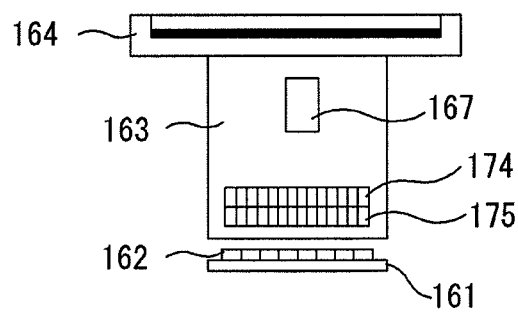
Figure 6:
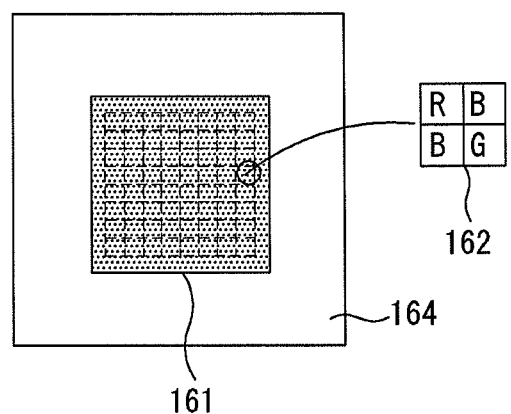

FIG. 5 shows yet another example of the back light module which is applied to this disclosure and configured to emit heat using a heat gun, and FIG. 6 shows further yet another example of the back light module which is applied to this disclosure and configured to use an ultraviolet/infrared light-emitting diode as a light-emitting diode.

Referring to FIG. 5, the back light module 160 is configured to emit heat using a heat gun 173. The back light module 160 may be implemented by coupling the heat gun 173 to the light-emitting tube 163 for emitting only light in FIG. 3. Hot air with a high temperature, emitted from the heat gun 173, flows in the light-emitting tube 163 via the heat tube 170, thus heating the light-emitting surface 165 over the light-emitting tube 170.

Alternatively, the back light module 160 shown in FIG. 5 may be coupled to the back light module shown in FIG. 4 and so may be used as a back light module for emitting heat and light at the same time. FIG. 4 shows the construction in which the heating coils 169 configured to generate heat using an externally applied power are formed in the light-emitting surface 165. If an indirect heating method using the heat gun 173 of FIG. 5 is added to the construction of FIG. 4, heat having a stronger intensity can be generated. However, since hot air emitted from the heat gun 173 may have an influence on the PCB 161, the back light module shown in FIG. 5 may further comprise a high temperature cutoff layer 172 on the bottom surface of the light-emitting tube 163 coming into contact with the PCB 161. Glass for high temperature shielding may be used as the high temperature cutoff layer 172. A heat sensor 171 may be further included in the light-emitting surface 165 of FIG. 5. The heat sensor 171 is described in detail later with reference to FIG. 8.

Referring to FIG. 6, the back light module 160 is configured to emit at least one of infrared rays and ultraviolet rays as well as light emitted from the light sources 162 formed in the PCB 161. The back light module 160 may be implemented by adding ultraviolet light sources 174 or infrared light sources 175 to the circumference of a lower wall of the light-emitting tube 163 shown in FIG. 3. The ultraviolet light sources 174 and the infrared light sources 175 may comprise ultraviolet light-emitting diodes and infrared light-emitting diodes, respectively. The ultraviolet light sources 174 or the infrared light sources 175 may have a desired luminous intensity with only the relatively small number because they have a luminous intensity higher than that of general light-emitting diodes. Meanwhile, although the ultraviolet light sources 174 and the infrared light sources 175 are formed in two stages in FIG. 6, only one of the ultraviolet light sources 174 and the infrared light sources 175 may be selectively used depending on the characteristic of the substrate 300 to be tested. Further, the ultraviolet light sources 174 and the infrared light sources 175 may be electrically coupled to the PCB 161 in which the light sources 162 are formed. The back light module 160 shown in FIG. 6 may also be coupled to the back light module 160 shown in FIG. 4 or 5.

Meanwhile, red (R), green (G), and blue (B) light-emitting diodes may be used as the light sources 162 of the back light module 160 as shown in FIG. 6. If the red (R), green (G), and blue (B) light-emitting diodes are used as the light sources 162 as described above, the electrical influence of a TFT can be measured by changing not only the intensity of radiation of back light, but also the spectrum of light. Accordingly, the electrical properties of the TFT can be measured more accurately. As described above, this document may comprise the ultraviolet light sources 174 and the infrared light sources 175. Accordingly, this document may measure the electrical properties of a TFT over a wider light region because it can generate not only the spectrum of a visible ray region, but the spectrum of an ultraviolet region or an infrared region. The back light module 160 shown in FIG. 6 may further comprise a heat sensor in the light-emitting surface 165. The heat sensor is described in detail below with reference to FIG. 8.

This document may further comprise a luminometer 123 configured to measure the luminance of light emitted from the back light module 160 in order to uniformly control the luminance of the back light module 160 and a feedback controller 180 configured to control the luminance of the back light module 160 at a preset level by comparing luminance within the luminometer 123 and luminance within the back light module 160. The photo sensor 167 or the heat sensor 171 is configured to transmit light detection information or heat detection information to the feedback controller 180. The feedback controller 180 controls the intensity of light or heat of the back light module 160 based on the detection information.

Figure 7:
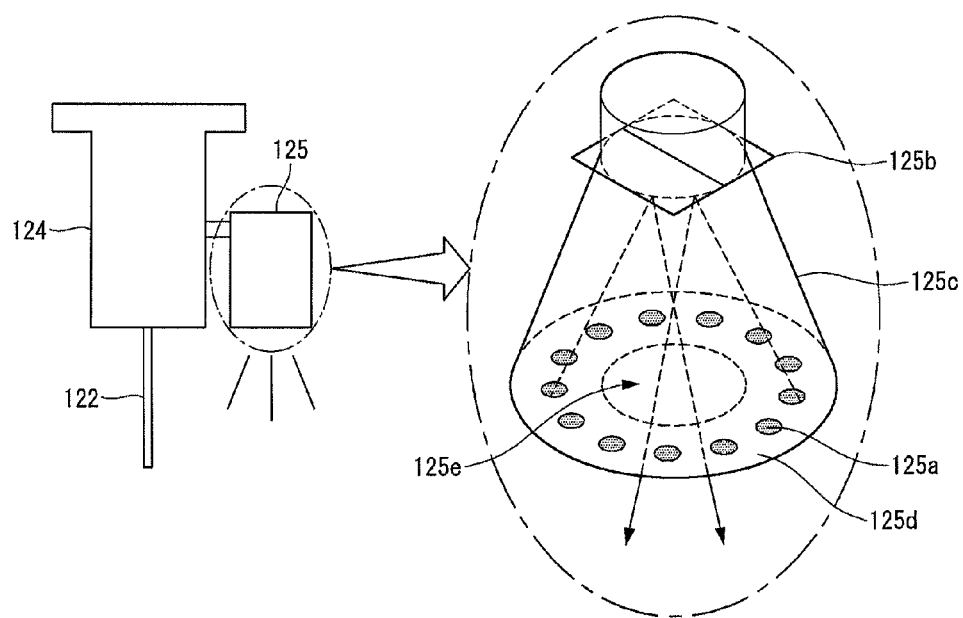
FIG. 7 is a diagram showing an example in which an upper light source unit is mounted on a probe head in the probe inspection apparatus of FIG. 1.

FIG. 7 is a diagram showing an example in which the upper light source unit is mounted on the probe head in the probe inspection apparatus of FIG. 1.

Referring to FIG. 7, the upper light source unit 125 is mounted on one side of the probe head 124 and is configured to comprise light source arrays 125a, a color filter plate 125b configured to reflect light, irradiated by the light source arrays 125a, toward the substrate in which the TFTs are formed and a body frame 125c configured to accommodate the light source arrays 125a and the color filter plate 125b. The upper light source unit 125 may further comprise a photo sensor.

The body frame 125c may have a cylindrical shape having an empty space and may have a skirt shape having a bottom diameter greater than a top diameter in order to widen the range of light irradiated. The body frame 125c comprises a light source support track 125d extending inwardly from its lower end and provides an attachment and detachment space to and from which the color filter plate 125b can be attached and detached on the light source support track 125d. The body frame 125c is made of material through which light cannot pass.

The light source arrays 125a are arranged on the light source support track 125d. Any one of a light-emitting diode, an ultraviolet light-emitting diode, and an infrared light-emitting diode may be used as a light source constituting the light source arrays 125. The intensity of radiation generated by the light source arrays 125 is controlled by a radiation measurement apparatus and a radiation control apparatus which may be placed outside the upper light source unit 125, so that the intensity of radiation can be controlled to a desired value. The radiation measurement apparatus and the radiation control apparatus may be replaced with some of the construction shown in FIG. 8.

The color filter plate 125b is configured to penetrate the body frame 125c and is placed on the light source arrays 125. The color filter plate 125b reflects light, irradiated by the light source arrays 125, toward a light emission hole 125e formed in the body frame 125c.

The upper light source unit 125 may be applied to a probe inspection apparatus different from the back light module shown in FIGS. 3 to 6 and may also be applied to a probe inspection apparatus along with the back light module shown in FIGS. 3 to 6.

The operation and effects of the upper light source unit 125 are described below.

First, this document provides an environment similar to an actual liquid crystal module state when the electrical properties of a TFT are tested using the upper light source unit 125 mounted on the probe head 124. In other words, in the actual liquid crystal module state, the TFT is greatly influenced by not only direct back light, but also light which is again incident on its channel unit after the light is reflected from the color filter through the TFT. Accordingly, the upper light source unit 125 of this document can implement this liquid crystal module state through the above construction.

Second, this document can enlarge a measurement range when only the back light module shown in FIGS. 3 to 6 is used using the upper light source unit 125 mounted on the probe head 124. In other words, if only the back light module shown in FIGS. 3 to 6 is used, the electrical properties of only TFTs corresponding to a position into which the back light module is inserted can be measured. However, if the upper light source unit 125 shown in FIG. 7 is used, the electrical properties of all TFTs can be measured irrespective of their positions.

Figure 8:
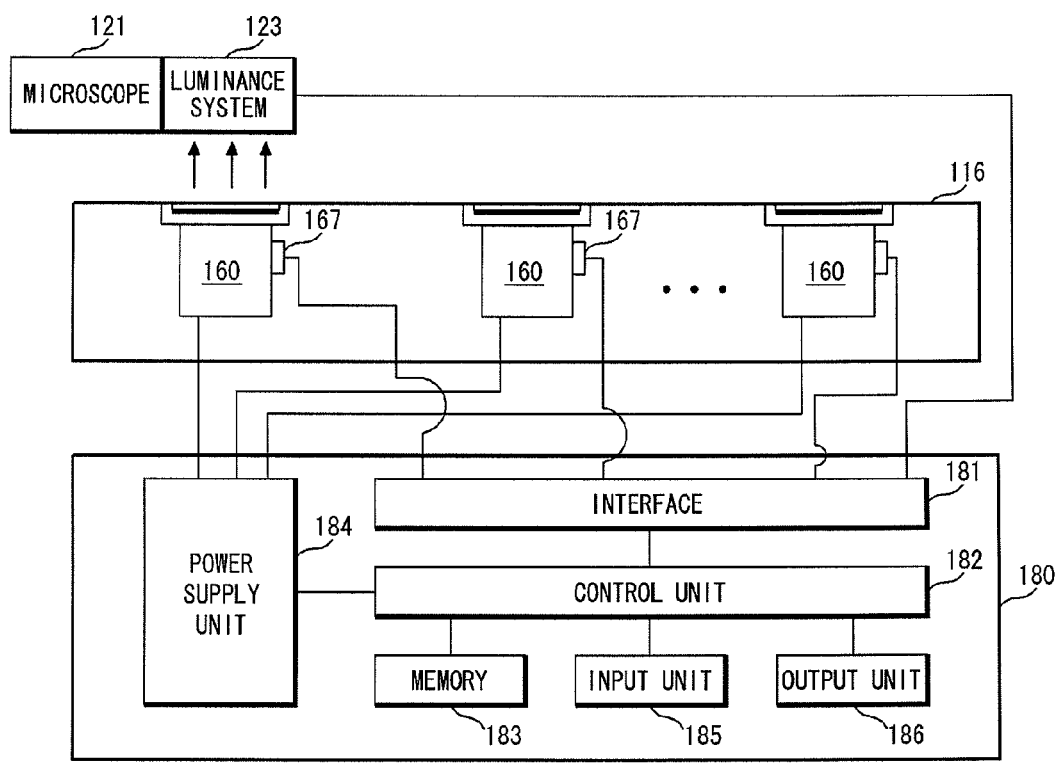
FIG. 8 is an exemplary view showing the configuration of a feedback controller and the back light module which are applied to this disclosure.

FIG. 8 is an exemplary view showing the configuration of a feedback controller and the back light module which are applied to this document.

Referring to FIG. 8, the feedback controller 180 comprises an interface 181 configured to perform communication with the luminometer 123 and the plurality of back light modules 160, memory 183 configured to store luminance information about the plurality of back light modules 160, a power supply unit 184 configured to supply electric power to the plurality of back light modules 160, a control unit 182 configured to compare luminance information received from the interface 181 and luminance information received from the memory 183 and to control the driving of the power supply unit 184 based on the comparison result, an input unit 185 configured to receive various pieces of information from a user, and an output unit 186 configured to output information received from the input unit 185 and various pieces of information controlled by the control unit 182. Here, each of the back light modules 160 may not comprise heating coils as shown in FIG. 3 or may comprise the heating coils 169 as shown in FIG. 4. Hereinafter, a luminance correction function for the light sources 162 is described apart from a process of supplying heat using the heating coils.

When the probe head 124 to which the luminometer 123 is attached moves to the central position of each of the back light modules whose luminance will be tested, the control unit 182 stores information about luminance on a surface of the back light module 160, received from the luminometer 123, and information about luminance received from the photo sensor 167 within the back light module 160, and driving information about electric power, which is induced based on the above luminance information and will be supplied to the back light module 160, in the memory 185. Here, if setting information about electric power to be supplied to each back light module is received through the input unit 185 in order to adjust the luminance of the back light module 160, the setting information, together with the above pieces of luminance information and driving information, may be stored in the form of an information table. Meanwhile, the above pieces of information stored in the above process may be used to correct the luminance of the back light module while the electrical properties for a substrate are tested and may also be used to correct the luminance of the back light module before the electrical properties for a substrate are tested.

In the case where the electrical properties for a TFT of the substrate 300 are substantially measured, the control unit 182 extracts information about a back light module to be tested, corresponding to the movement coordinates of the probe head 124, receives internal luminance information about the back light module 160 to be tested from the photo sensor 167 of the back light module 160 to be tested, receives external luminance information about the back light module 160 to be tested from the luminometer 123, compares the external luminance information or the internal luminance information with the above information table, extracts voltage/electric current values necessary to maintain a uniform luminance of the back light module to be tested, and controls the power supply unit 184 based on the extracted values.

The power supply unit 184 supplies the back light module 160 to be tested with electric power corresponding to the extracted values under the control of the control unit 182. Accordingly, the back light module 160 can emit a uniform and ideal luminance while the electrical properties for the substrate are being measured. In other words, the control unit 182 analyzes luminance values measured inside and outside the light-emitting tube 163. If the intensity of radiation is lower than or higher than a reference value, the control unit 182 outputs correction voltage/electric current values through the power supply unit 184. Accordingly, the light sources 162 can maintain a constant intensity of radiation within a certain range. Although the luminance correction function using the light sources 162 has been described above, a luminance correction function or a spectrum correction function may also be performed using the ultraviolet light sources 174 and the infrared light sources 175.

Further, this document can implement a temperature correction function using the heating coils 169 or the heat gun 173 based on the heat sensor 171. That is, if the heat sensor 171 corresponding to the photo sensor 167 and a thermometer corresponding to the luminometer 123 are provided, this document can control the temperature of the back light module 160 using the feedback controller 180. However, although the a thermometer is not provided, this document can control the temperature of the back light module based on only temperature information detected by the heat sensor 171.

According to the above-described document, a user can measure a change in the electrical properties for the entire region of a substrate for a liquid crystal display, and the back light module capable of providing adjustment for the uniformity of light and the intensity of radiation, the intensity of radiation necessary for measurement, and heat for temperature rise is included. Accordingly, heat and light can be provided to the substrate at the same time, and at least one of a change in the luminance of the back light module, a change in the spectrum, and a change in the temperature can be corrected. Consequently, the reliability of measurement in a change in the electrical properties of a substrate, caused by light and heat, can be enhanced. In other words, according to this document, the back light module which can be controlled and is stabilized is embedded within the stage 116 of the probe inspection apparatus. Accordingly, test data for a substrate can be acquired in a similar condition to an actual state in which a liquid crystal display is used.

Figure 9:
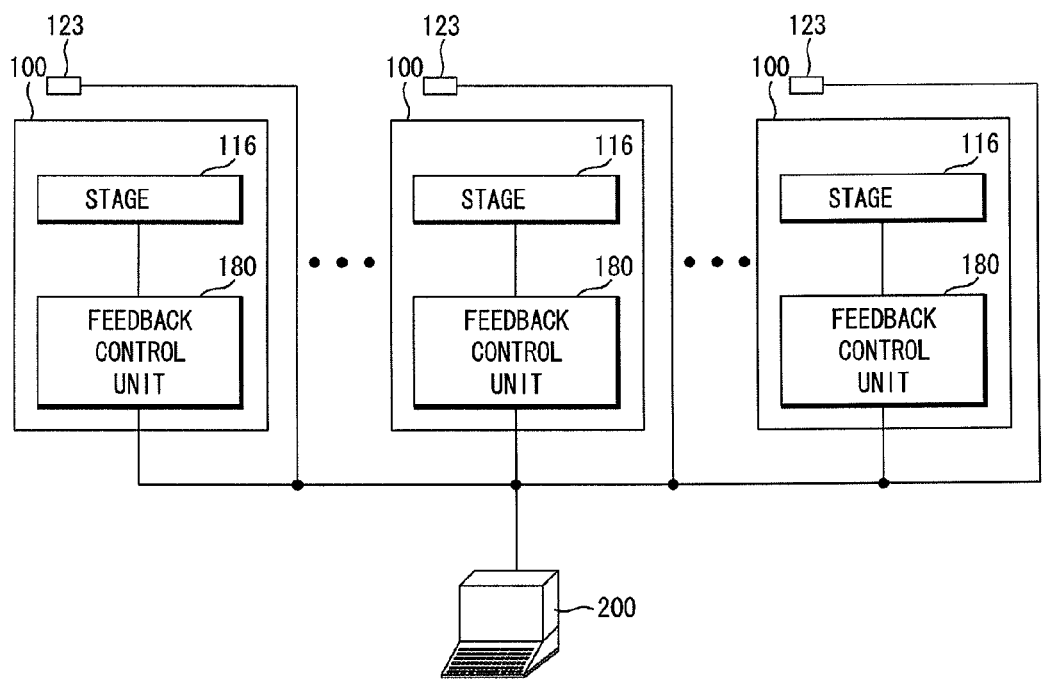
FIG. 9 is an exemplary view showing a state in which a number of the probe inspection apparatuses according to this disclosure are used.

FIG. 9 is an exemplary view showing a state in which a number of the probe inspection apparatuses according to this document are used. This figure shows a state in which the luminance of the back light module of a plurality of probe inspection apparatuses 100 is controlled using the feedback controllers 180 of FIG. 8.

Referring to FIG. 9, in the case where the plurality of probe inspection apparatuses 100 is used within a process chamber, the feedback controllers 180 provided in the respective probe inspection apparatuses 100 may be provided in the supporter 150, and a user terminal 200 capable of controlling the feedback controllers 180 at the same time may be installed at a separate place.

Luminance values or temperature values outside the back light module, received from the luminometer 123 or the thermometer coupled to the respective probe inspection apparatuses 100, may be transmitted to the user terminal 200 via the probe inspection apparatuses or may be directly transmitted to the user terminal 200. The user terminal 200 controls the feedback controllers 180 provided in the respective probe inspection apparatuses 100 so that luminance values or temperature values of all the back light modules can be maintained equally.

To this end, the user terminal 200 stores information about the probe inspection apparatuses 100, information about the feedback controllers 180 included in the respective probe inspection apparatuses, and information about each of the back light modules and also stores control information about each of the back light modules. The user terminal 200 is configured to extend the function of the feedback controller 180 and to prevent a change in the measured electrical properties (values) of a substrate according to the probe inspection apparatus by maintaining the same luminance or temperature for all back light modules.

Meanwhile, a CCFL and a light-emitting diode used as the back light of a liquid crystal display operates as an on-and-off light having a specific frequency and waveform, and the frequency and waveform differs depending on the model of the liquid crystal display. Accordingly, the probe inspection apparatus has to comply with the frequency and on-and-off waveform. Accordingly, this document may add a power modulation function to the control unit 182 of the feedback controller 180 so that the power supply unit 184 can implement a frequency and waveform used to drive the back light of an actual liquid crystal display. The control unit 182 which is applied to this document may receive information about a frequency, waveform, etc., which are actually used to drive a liquid crystal display, from the input unit 185, store analyzed information in the memory 183, and, when the electrical properties for a substrate for the liquid crystal display are tested, control the power supply unit 184 based on the frequency and waveform information stored in the memory 183. Accordingly, this document may obtain a more accurate electrical property value for a substrate because it uses the frequency and waveform of electric power, actually supplied to a liquid crystal display, even when a test for the electrical properties of the substrate is performed.

Figure 10:
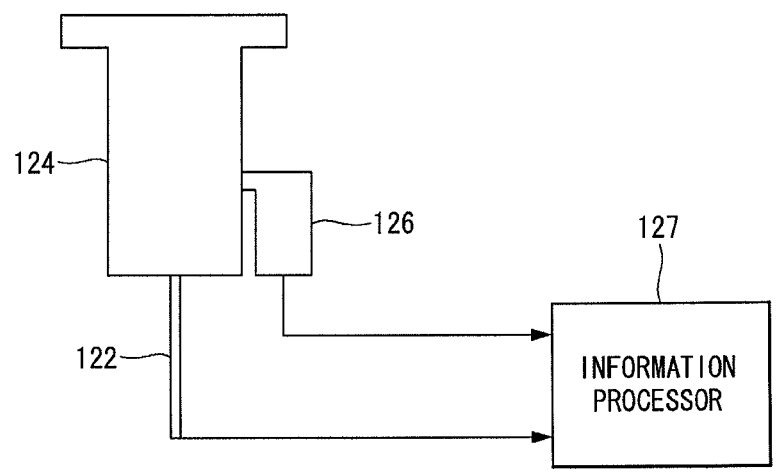
FIG. 10 is a diagram showing an example in which a microscope and an information processor are added to the probe inspection apparatus of FIG. 1 in order to measure the channel width (W)/channel length (L) of a TFT.
Figure 11:
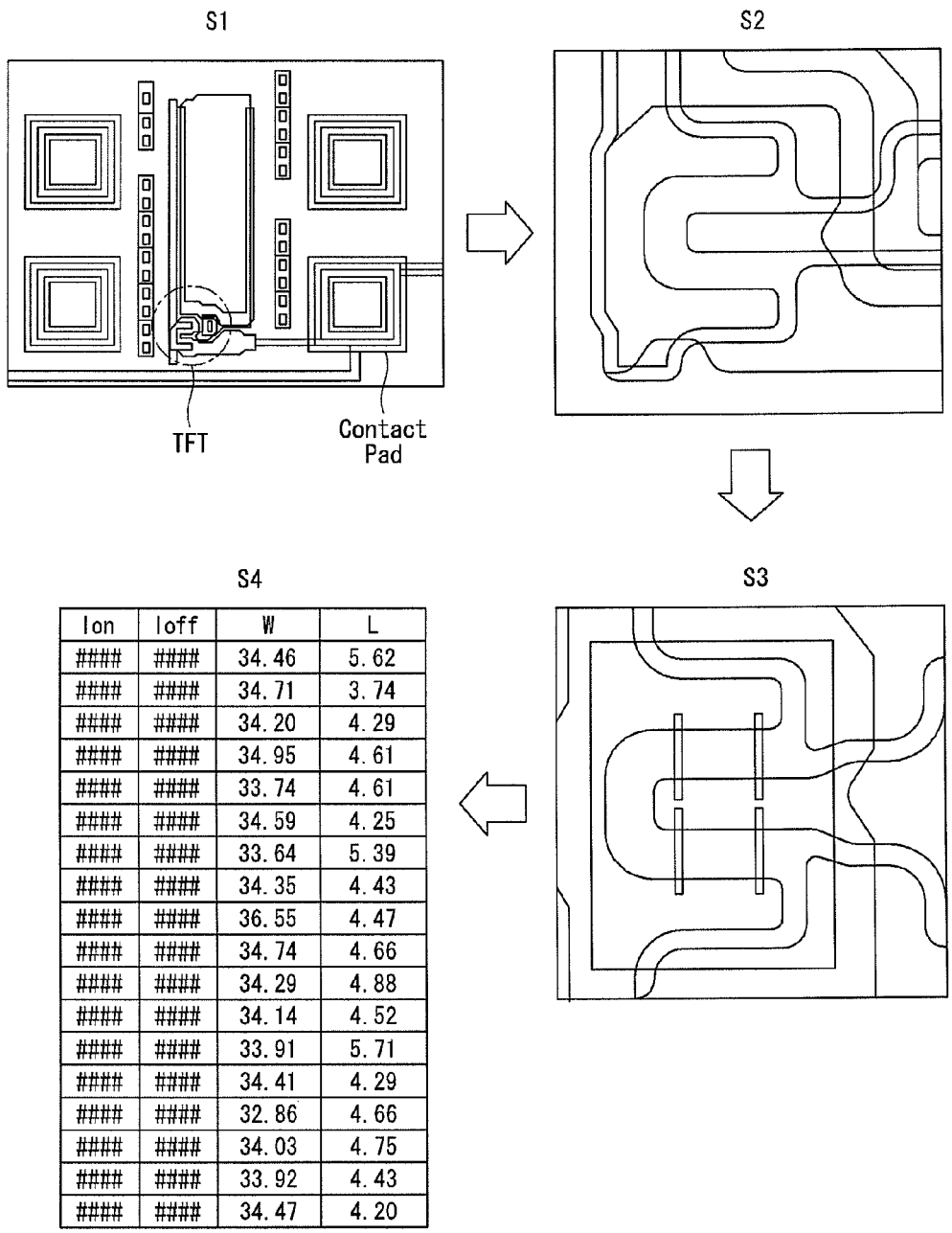
FIG. 11 is a diagram showing the operation of the probe inspection apparatus of FIG. 10, which is performed step by step.

FIG. 10 is a diagram showing an example in which a microscope and an information processor are added to the probe inspection apparatus of FIG. 1 in order to measure the W/L of a TFT, and FIG. 11 is a diagram showing the operation of the probe inspection apparatus of FIG. 10, which is performed step by step.

Referring to FIG. 10, the probe inspection apparatus 100 further comprises the microscope 126 mounted on one side of the probe head 124 and the information processor 127 configured to process information obtained through the contact of the probe pin 122.

The microscope 126 provides an image for the W/L of a TFT on which a test for electrical properties is being performed. Wherein, 'W' denotes a width of channel unit, and 'L' denotes a length of channel unit. To this end, the microscope 126 may have a high magnifying power×100.

The information processor 127 measures the W/L value of the TFT based on the image acquired by the microscope 126, creates an image file including the measured value, calculates a process deviation (CD) of the TFT through the image file by executing a built-in program, and analyzes a correlation between the W/L of the TFT and an electric current flowing through the TFT by mapping the electrical property information of the TFT, acquired through the contact of the probe pin 122, and the calculated data.

The operation of the probe inspection apparatus is described below with reference to FIG. 11. When the probe head 124 is placed on a corresponding TFT and so a contact pad for the TFT comes into contact with the probe pin 122, the microscope 126 measures a channel unit image of the TFT at steps S1 and S2.

Information about the electrical property of the TFT, acquired through the contact of the contact pad and the probe pin 122, and information about the channel unit image of the TFT acquired through the microscope 126 are supplied to the information processor 127. The information processor 127 measures the W/L value of the TFT based on the information about the channel unit image of the TFT, creates an image file including the measured value, and then calculates a process deviation (CD) of the TFT using the image file by executing a built-in program at step S3.

Next, the information processor 127 analyzes a correlation between the W/L of the TFT and an electric current, flowing through the TFT, by mapping the calculated data and the electrical property information about the TFT, acquired through the contact of the contact pad and the probe pin 122, and provides a user with a characteristic analysis value of the TFT, including the calculated result a step S4.

According to this probe inspection apparatus, this document can analyze the degree of distributions of a process deviation (CD) of a TFT within a substrate and acquire very accurate characteristic information about the circuit patterns of the substrate based on a correlation between an electric current (i.e., the electrical property value of the TFT) and the W/L of the TFT.

While this document has been described in connection with what is presently considered to be practical exemplary embodiments, it is to be understood that this document is not limited to the disclosed embodiments, but, on the contrary, is intended to cover various modifications and equivalent arrangements included within the spirit and scope of the appended claims.

The invention claimed is:

1. A probe inspection apparatus, comprising:
a base plate;
a stage placed over the base plate and comprising a plurality of back light modules that supply a rear surface of a substrate with at least one of light or heat, the substrate being seated in the stage;
a probe pin configured to electrically come into contact with circuit patterns formed in the substrate and measure electrical properties of the circuit patterns;
a probe head configured to support the probe pin and move in an X or Y axis; and
an upper light source unit mounted on one side of the probe head and configured to irradiate light to the circuit patterns,
wherein the upper light source unit comprises light source arrays, a color filter plate placed on the light source arrays and configured to downwardly reflect light generated by the light source arrays, the color filter plate is applied as one color filter layer in an actual liquid crystal module state, a light source support track into which the color filter plate is inserted and on which the light source arrays are mounted, and a light emission hole configured to introduce the reflected light to the circuit patterns.

2. The probe inspection apparatus of claim 1, wherein each of the back light modules comprises:
a plurality of light sources configured to generate light;
a light-emitting surface comprising a spread sheet and that uniformly irradiates light from the light sources to the rear surface of the substrate;
a light-emitting tube configured to provide a light passage between the light sources and the light-emitting surface; and
a support frame configured to support the light-emitting surface.

3. The probe inspection apparatus of claim 1, further comprising:
a luminometer mounted on the probe head and configured to measure a luminance of light supplied from the upper light source unit or the back light modules; and
a feedback controller configured to compare a luminance information received from the luminometer and a luminance information received from the upper light source unit or the back light modules and control a brightness of the upper light source unit or the back light modules to a constant level.

4. The probe inspection apparatus of claim 1, further comprising:
a heat sensor formed in each of the back light modules and configured to detect a temperature of the back light module; and
a feedback controller configured to compare preset temperature information and heat detection information received from the heat sensor and control a heating temperature of the back light module to a constant level.

5. The probe inspection apparatus of claim 3, wherein the feedback controller comprises:
an interface configured to perform communication with the luminometer and the back light modules;
memory configured to store driving information about the back light modules;

a power supply unit configured to supply electric power to the plurality of back light modules; and a control unit configured to control a power level of the power supply unit in order to constantly maintain the brightness of the back light modules based on the luminance information, received from the luminometer and the back light modules, and the driving information, received from the memory, via the interface.

6. The probe inspection apparatus of claim 3, wherein the feedback controller is in common coupled to a user terminal along with feedback controllers of other probe inspection apparatuses and is configured to control luminance of the back light modules under the control of the user terminal.

7. The probe inspection apparatus of claim 3, wherein the feedback controller is configured to receive information about a frequency and waveform used to drive a back light of a liquid crystal module, modulate and store the receive information, and control the luminance of the back light modules based on the frequency and waveform information.

8. The probe inspection apparatus of claim 2, wherein heating coils configured to emit heat according to an application of electric power are provided in the light-emitting surface.

9. The probe inspection apparatus of claim 2, wherein a heat tube configured to receive external hot air having a high temperature is provided in the light-emitting tube.

10. The probe inspection apparatus of claim 2, wherein at least one of an ultraviolet light source configured to emit ultraviolet rays and an infrared light source configured to emit infrared rays is provided on an internal side of the light-emitting tube.

11. The probe inspection apparatus of claim 2, wherein the light sources comprise a red light-emitting diode, a green light-emitting diode, and a blue light-emitting diode.

12. The probe inspection apparatus of claim 1, further comprising:

a microscope mounted on the other side of the probe head and configured to provide an image of a channel unit width (W)/length (L) of each of the circuit patterns; and an information processor configured to measure a W/L value based on the image acquired by the microscope, create an image file including the measured W/L value, calculate a process deviation of the circuit pattern using the image file by executing a built-in program, and output a correlation between the W/L value and an electric current flowing through the circuit pattern by mapping information about electrical properties of the circuit patterns which are acquired through a contact of the probe pin, on the calculated process deviation.

* * * * *